(12) United States Patent
Mahrenholtz et al.

(10) Patent No.: US 7,813,839 B2
(45) Date of Patent: Oct. 12, 2010

(54) PROCESS FOR CONTROLLING A PRODUCTION PROCESS

(75) Inventors: Jochen Mahrenholtz, League City, TX (US); Stefan Wershofen, Mönchengladbach (DE); Gerhard Then, Dormagen (DE); Sabine Pegel, Düsseldorf (DE); Jun Wang, Ratingen-Hösel (DE); Erman Sevinc, Camlipark (TR); Richard H. Guhl, Houston, TX (US)

(73) Assignee: Bayer MaterialScience AG, Leverkusen (DE)

( * ) Notice: Subject to any disclaimer, the term of this patent is extended or adjusted under 35 U.S.C. 154(b) by 374 days.

(21) Appl. No.: 11/656,283

(22) Filed: Jan. 22, 2007

(65) Prior Publication Data

US 2008/0147208 A1 Jun. 19, 2008

Related U.S. Application Data

(63) Continuation-in-part of application No. 11/638,817, filed on Dec. 14, 2006, now abandoned.

(51) Int. Cl.
*G05B 21/00* (2006.01)
*C07C 263/10* (2006.01)

(52) U.S. Cl. .............. 700/273; 700/266; 700/270; 700/268; 560/347

(58) Field of Classification Search ............... 700/28, 700/266, 268–270, 271, 273; 560/347, 330, 560/336, 341, 338
See application file for complete search history.

(56) References Cited

U.S. PATENT DOCUMENTS

| 4,128,569 | A  | * | 12/1978 | Horn et al. | 560/347 |
| 4,332,590 | A  |   | 6/1982  | Smith       |         |
| 5,925,783 | A  |   | 7/1999  | Jost et al. |         |
| 6,916,953 | B2 | * | 7/2005  | Walsdorff et al. | 560/341 |
| 2007/0232827 | A1 | * | 10/2007 | Wolfert et al. | 560/347 |
| 2008/0200722 | A1 | * | 8/2008  | Wolfert et al. | 560/347 |

FOREIGN PATENT DOCUMENTS

WO    WO96/16028    * 5/1996

* cited by examiner

*Primary Examiner*—Albert DeCady
*Assistant Examiner*—Steven R Garland
(74) *Attorney, Agent, or Firm*—Lyndanne M. Whalen; Noland J. Cheung (57) ABSTRACT

A production process such as an isocyanate production process, conducted with a production facility having (a) at least two incoming streams, b) at least one exit stream and c) at least one inner recycling stream is controlled by adjusting at least one incoming stream amount by means of regulating controls to control the exit stream concentration and/or amount.

42 Claims, 6 Drawing Sheets

PROCESS FOR CONTROLLING A PRODUCTION PROCESS

The present application is a continuation-in-part of, and claims the benefit of prior Application Ser. No. 11/638,817, filed Dec. 14, 2006 now abandoned.

TECHNICAL FIELD

The invention relates to a production facility such as an isocyanate production facility and a method for controlling a production process which includes at least one inner recycling stream. This method enables easy optimization of the entire process with respect to quantity and quality of the product and a reduction in production costs.

BACKGROUND OF THE INVENTION

In known isocyanate production facilities, a phosgene solution and an amine solution are introduced into a reactor where the phosgene and amine react to form an isocyanate. The reaction products are generally separated in a distillation column to obtain purified isocyanate and often further purified in a distillation or crystallization unit to separate its isomers. In order to ensure production of a predetermined amount of the isocyanate, the amount of phosgene and of amine introduced into the reactor and/or column is controlled. Further, to ensure production of isocyanate satisfying predetermined quality requirements, the process parameters of the reactor such as pressure and temperature are controlled. The distillation column used to separate the materials in the reacted reaction mixture is designed so that the isocyanate separated in that column will be obtained in the required amount and quality from the reacted reaction mixture. It is possible to calculate the optimal process parameters for the isocyanate production process in the steady state. These calculated process parameters are taken as controlled variables to automatically keep them relatively constant in case of an unsteady disturbance. Generally, it is possible to control every controlled variable independently of the others. When, for example, the temperature of the distillation column decreases due to cold weather, the amount of heat for the distillation column is increased to keep the optimized reference temperature of the distillation column constant.

It is preferred to feed excess phosgene to the reactor in order to influence the chemical equilibrium of the reactor contents and to maximize the isocyanate output. Since phosgene is a highly toxic and harmful gas, the excess phosgene must be eliminated after the reaction is complete. Alternatively, the excess phosgene may be recycled to the reactor and thereby increase cost effectiveness. The solvent obtained in the distillation step can also be recycled. However, use of recycled phosgene and solvent may cause the isocyanate production process to become unstable. Since unavoidable variations of the process parameters affect the amount, the pressure, the temperature, the concentration (quality) etc. of the recycled phosgene and solvent, variations in the process parameters and disturbances may even increase when automatic control of the process parameters is attempted. Due to the recycling, nearly every process parameter influences nearly all other process parameters. Thus, it is necessary to manually set a number of reference parameters based on the overall situation to avoid major variation of the amount and quality of the product isocyanate. Due to the potential for large variation of the isocyanate product quality, conservative reference parameters are set for the isocyanate production process to ensure a minimum quality of the isocyanate. This results in a difficult and complicated process control and high costs.

It is an objective of the present invention to facilitate the process control of a production process, particularly, an isocyanate production process. It is a further objective to reduce variations in the product, e.g., isocyanate, to increase the product output, and to reduce the production costs. Furthermore, it is an objective to improve and/or increase automation of the production process. It is another objective of the present invention to increase the stability of the automated process control while the amount of unused reactant, e.g., phosgene, and spent solvent is preferably reduced. Moreover, the amount of unwanted substances in the production process should be reduced.

SUMMARY OF THE INVENTION

The above-mentioned objectives are achieved by the process for controlling a production process, particularly, an isocyanate production process, of the present invention. In the production processes controlled in accordance with the present invention, more than one incoming stream, at least one exit stream and at least one inner recycling stream are employed. In an isocyanate production process, the incoming streams generally include: (1) a phosgene stream composed primarily of phosgene and (2) a solvent feed stream largely made up of a solvent. In addition to several plant-wide regulating controls, controls for the amount of the phosgene stream and the amount of the solvent feed stream are included to permit adjustment of the concentration and the amount of the exit stream.

DETAILED DESCRIPTION OF THE PREFERRED EMBODIMENTS OF THE INVENTION

The present invention is directed to a method for controlling a production process. While this invention can be applied to any production process, it will be described in greater detail with respect to an isocyanate production process.

In the production of an isocyanate in accordance with the present invention, more than one incoming stream, at least one exit stream and at least one inner recycling stream are employed. The incoming streams include: (1) a phosgene stream composed primarily of phosgene and (2) a solvent feed stream largely made up of a solvent. In addition to several plant-wide regulating controls, controls for the amount of the phosgene stream and the amount of the solvent feed stream are included to permit adjustment of the concentration and the amount of the exit stream.

It has surprisingly been found that setting the amount of the phosgene stream and the amount of the solvent feed stream as the principal controlled variables for the plant results in plant-wide optimization, when all other units of the isocyanate production facility are each preferably controlled independently of each other. Thus, a 2×2-system is sufficient for plant-wide optimization. The other process parameters of the controlled process are of less importance for optimization because their impact on the composition of the exit stream is lower than that of the amounts of phosgene and solvent. The different subsystems of the isocyanate production process can therefore be controlled independently of each other. Thus, it is possible to partially automate every subsystem in which the reference variables may be determined by calculation and the process parameters optimized. The relationship of the phosgene stream and the solvent feed stream to the exit stream enables a simplified control of the production process because the number of variables to be checked by a sophisticated underlying control system is significantly reduced. The other process parameters are automatically set by the control method in accordance with the present invention. Since the variation in the amount and the variation of the quality (concentration) of the exit stream are reduced by the process of the present invention, it is possible to use improved reference parameters leading to an improved isocyanate output. Because substantially all unused solvent and phosgene can be recovered by the inner recycling stream, the amount of purged phosgene and solvent can be minimized and the production costs decreased. Moreover, the control method is stable according to the Nyquist criterion.

In a preferred embodiment of the present invention, the phosgene stream is fed to a solution unit to generate a phosgene solution stream. A second stream (referred to hereinafter as the amine solution stream) which is a mixture of an amine and a solvent is combined with the phosgene solution stream. The content of amine in the amine solution stream is $\geq 15\%$ and $\leq 95\%$, preferably $\geq 15\%$ and $\leq 85\%$ by weight, based on the combined weight of solvent and amine in this amine solution stream. The content of phosgene in the phosgene solution stream is $\geq 15\%$, preferably $\geq 20\%$ and most preferably $\geq 30\%$ by weight, based on the combined weight of solvent and phosgene in this stream. The ratio of amine solution stream and phosgene solution stream is such that at least the stoichiometric amount of phosgene for the reaction of the amino groups present in the amine solution stream is provided; that is, one mole of phosgene is present per mole of amino groups present in the amine solution stream. Preferably, an excess of phosgene is provided based on the amino groups present in the amine solution stream; that is, more than one mole of phosgene is present per mole of amino groups present in the amine solution stream.

The combined stream is fed to a reactor. The reactor is equipped to accommodate at least one inner recycling stream, e.g., a recycle stream composed primarily of phosgene and/or solvent and/or HCl. The recycle stream(s) and a product stream which is primarily isocyanate and, optionally, solvent are produced in the reactor. The product stream is separated from the reaction mixture by a separator into at least one exit stream composed mainly of isocyanate and at least one stream composed mainly of solvent. The solvent feed stream is fed to the recycle stream in a recovery unit for recovering phosgene and a recovery stream is fed from the recovery unit to the solution unit. The several streams may be directly or indirectly (e.g., via another stream, unit or subunit) fed to its designated unit.

It has surprisingly been found that control of the solution unit as supervisory control leads to plant-wide control. Treating the solution unit as key unit for a plant-wide optimization leads to a simplified control concept easy to design and, if necessary, easy to adapt to changed conditions. For the recovery unit, the controlled amount of the solvent feed stream is a reference variable and for the solution unit, the controlled amount of the phosgene stream is a reference variable.

Where units other than the solution unit such as the reactor, the separation unit, the recovery unit, etc. are controlled virtually independent of each other, the amount and the quality (concentration) of the exit stream containing the wanted product can be determined by calculation on the basis of the quality, temperature and level of the solution unit, i.e., parameters which can be measured substantially in situ. These other units (i.e., units other than the solution unit) may be controlled by setting pressure, temperature and/or level based on the concentration and/or amount of its outgoing stream. Further, the level may be controlled by a feed forward control based on the amount of a feed stream. Additional regulatory controls may also be employed. For example, the viscosity of one of the at least one exit streams may be controlled by adjusting pressure and temperature of the separation unit or subunit.

Surprisingly, control of the phosgene stream and the solvent feed stream leads to a nearly steady state reaction in the reactor although recovery of recycled phosgene, dissolving in the solution unit and mixing with dissolved amine take place prior to feeding the phosgene and solvent streams to the reactor. Since the desired amount and quality of the exit stream is known, the requirements for the separation unit can be calculated, which in turn enables calculation of the reactor requirements and to calculation of the requirements for the solution unit controlled by the master process control in accordance with the present invention. In the general operation mode, the quality of the exit stream is determined by the formulation for the reaction and the amount of isocyanate produced is determined by the amount of the amine in the amine stream. Thus, the output of the isocyanate production process depends on the preset flow rate (amount) of amine. The weight ratio of solvent to amine in the combined stream can be $\leq 10$, preferably $\leq 8$, most preferably, from 2 to 7.

The process can be automatically driven and automated by control of the solution unit. Disturbances which are not eliminated in the solution unit are detected so quickly that the regulatory controls of the subsequent units (e.g., the reactor and/or separation unit (separator)) can be adjusted in advance to eliminate any potential effect of these disturbances. It is also preferred that nearly all units and/or subunits be adjusted in advance when a disturbance is known to be occurring. For example, when the output of the exit stream is to be changed, the appropriate amount of amine may be calculated and the appropriate adjustment of the controls of the units and/or subunits of the isocyanate production facility in advance (e.g., adjustment of the levels, temperatures, etc.) to eliminate foreseeable disturbances and prevent exceeding maximum or minimum values may be made. The adjustment of the controllers in advance to accommodate a foreseeable change in conditions results in improved stability.

Every unit or subunit used in the production of the isocyanate may be integrated into a single device. For example, the solution unit may be a single stand-alone solution tank or it may be integrated in the recovery unit as absorber bottom or the like. Further, every unit or subunit may be made up of multiple subunits arranged in sequence and/or in parallel for achieving the desired effect or for performing the desired function. For example, the reaction may be performed in several steps in different reactors coupled to each other. It is also possible to perform the separation in different subunits of the separation unit to increase the quality of the separated streams, if necessary. Where a unit is made up of several subunits, every subunit may have its own regulatory control. The regulatory control of the whole unit is preferably adjusted so that the different subsystems are operated at optimized conditions. For example, a very low level in a first subsystem and a very high level in a second subsystem at the same time are prevented by the control for the whole unit. The incoming and outgoing streams of this unit stay unchanged while the inner streams of the unit are changed to save energy, steam, cooling, etc. thereby increasing, e.g., the thermal efficiency.

To control the process parameters of the isocyanate production process and the subsystems within that process, the following control concepts can be achieved by appropriately designed controllers: continuous feedback control, discrete feedback control, disturbance feed forward, load feed forward, minimum/maximum selection, single-variable controllers, multivariable controllers, lead/lag control, model-based control, controller and control structure selection, interactions (RGA=relative gain array), directionalities (SVD=singular value decomposition), status estimators, online simulation, status controllers, parameter identification, internal model control, model predictive control, gain scheduling, single input multiple output control, range control, override control, multiple input single output control, mixed value control, multiple input multiple output control, decentralized control, decouplers, adaptive control, disturbance compensation, disturbance controllers, cascade controllers, single-variable PID controllers (PID controller=proportional-integral-derivative controller), anti-windup control, structure changeovers, pre-filters, ratio control, split-range control, deadtime controllers, single variable P (P=proportional) and PI (PI=proportional-integral) controllers, and signal filters. Preferably, combinations of simple and complex control concepts and/or partial automation concepts are employed.

The process described can be applied to the production of a wide variety of organic isocyanates. The isocyanate may be MDI, that is, an isocyanate or mixture of two or more isocyanates of the diphenylmethane series as depicted in the following formula:

The isocyanate may also be TDI, that is, 2,4-diisocyanato toluene, 2,6-diisocyanato toluene or mixtures of 2,4-diisocyanato toluene and 2,6-diisocyanato toluene; HDI, that is, 1,6-hexamethylene diisocyanate; or IPDI (isophorone diisocyanate).

The starting amine may be MDA, that is, an amine or mixture of two or more amines of the diphenylmethane series as depicted in the following formula:

The starting amine may also be TDA, that is, 2,4-diamino toluene, 2,6-diamino toluene or a mixture of 2,4-diamino toluene and 2,6-diamino toluene; HDA, that is, 1,6-hexamethylene diamine; or IPDA (isophorone diamine).

The solvent may be selected from any of the known aliphatic, aromatic or araliphatic hydrocarbons, chlorinated aliphatic, aromatic or araliphatic hydrocarbons (e.g., chlorobenzene (MCB) or 1,2-dichlorobenzene (ODB)), and any other solvent which is known in the art as solvent for the phosgenation of amines or mixtures containing two or more of the above-mentioned solvents.

The reactor for conducting the isocyanate-forming reaction may include additional subsystems to ensure the desired quality. The separator is preferably a distillation unit which may include more than one distillation step. The separator, particularly the separator for purifying the solvent, may include a condensation unit (e.g., a stripper). Since the solubility of phosgene in the solvent is better at lower temperatures and higher pressures the recovery unit may comprise one or more condenser and one or more absorber. Further, the recovery unit may be pressurized by an inert gas (e.g., Helium). The exit streams may be connected to a post process unit. By means of the post process unit, the isocyanate in the exit stream may be further treated. For example, the isocyanate may be separated into a stream composed mainly of isocyanate polymers and a stream composed mainly of isomers of isocyanate monomers.

Every stream may be composed of one or more subunits, e.g., a buffer tank, a heat exchanger, a valve, a cooler, a heater, a condenser, and a steam inlet. In order to collect enough information for the automated control, every unit and every stream may include detecting devices for measuring process parameters such as temperature, pressure, concentration (quality), flow rate, level, feed rate, and outlet rate. In addition, every unit and every stream may include an appropriate control device (controller) to control the measured process parameters by influencing (preferably directly) the controlled process parameter.

In a preferred embodiment of the present invention, the change of the amount of the solvent stream is adjusted to a certain ratio with a target amount of the phosgene feed stream which is calculated based on the amount of the amine feed stream. This ratio is determined by the concentration of the phosgene solution through a feedback controller. Adjustment of the solvent feed stream is prior to and/or faster than the targeted change of the amount of the phosgene stream. Additionally, the amount of the solvent stream is adjusted based on the recycled phosgene stream. This control safeguards the stability of the solution unit control. It was surprisingly found that the level and the concentration of the solution unit depend in a nonlinear manner on the amount of the phosgene stream and the amount of the solvent feed stream. It is even possible that the direction of the dependence changes. For instance, increasing the solvent feed stream one time leads to an increased level and another time to a decreased level of the solution unit. This non-linear dependency renders stable control of the solvent unit nearly impossible or at least very complicated because a lot of information has to be processed for controlling the solvent unit. However, it has been found that the nonlinearity depends on the amount of recycled solvent. Due to the control based dependency of the amount of phosgene stream to the amount of the solvent feed stream, the nonlinear effect of the recycled solvent can be equalized. This control strategy enables stable control by a controller easy to design and can be realized using common methods known to people skilled in the art.

Preferably, the amount of the solvent feed stream is adjusted to a certain ratio with the amount of phosgene in the recycle stream as well as the amount of produced phosgene. The amount of phosgene in the recycle stream is calculated using the variation in time of the amount of the phosgene stream, the variation in time of the amount and concentration of the mixture stream and the reaction kinetics of the reactor. Due to this control strategy, it is possible to react very fast to a change in the amount of phosgene in the recycle stream and the phosgene production. The calculation of the phosgene amount in advance enables better anticipation of the expected situation in the recovery unit. This knowledge makes it possible to adjust the amount of the solvent feed stream in advance, so that unsteady dynamics in the production process can be prevented or at least reduced. Since the reaction kinetics and the amount and concentration of the mixture stream are given, it is in most cases sufficient to store the measured amount of the phosgene stream in a storing device for calculating a good correction variable for the solvent feed stream in order to minimize purged phosgene. If a change of the amount and concentration of the mixture stream is intended, the variation in time of these process parameters can be stored, too.

Since the recycle stream causes strong interactions between the process units/subunits, the amount of phosgene in the recycle stream and the concentration of the solvent in the recycle stream are preferably kept constant. Regulatory controls for the temperature and pressure of the recycle stream can be used to minimize such interactions and disturbances.

Preferably, the solution unit is made up of more than one solution unit control. The first solution unit control includes a control for the solvent concentration in the solution unit depending on a change of the amount of the solvent feed stream, a control for the solution temperature, e.g., by controlling the heat exchanger(s), and a control for the level of the solution unit depending on a change of the amount of the phosgene stream. A second solution unit control includes a control for the solvent concentration in the solution unit depending on a change of the amount of the phosgene stream and a control for the level of the solution unit depending on a change of the amount of the solvent feed stream. The ratio used to calculate changes of the solvent concentration and level in the solution unit control depends on the frequency of the change of the amount of the solvent feed stream and/or of the change of the amount of the phosgene stream. At a lower frequency, e.g., nearly steady state, the ratio of the first solution unit control is higher and at a higher frequency, e.g., at disturbances, the ratio of the second solution unit control is higher. It has been found that the first solution unit control is more stable at low disturbance frequencies and the second solution control is more stable at high disturbance frequencies. For that reason, the stability is increased by taking this frequency dependence into account. The nonlinear relationship of the solvent feed stream to the level of the solution unit must also be considered when designing the controller and selecting the control structure. Since the channels of these control problems are strongly coupled, a multivariable controller or a similar control structure is preferred. Depending on the frequencies, the multivariable controller adapts the gains and amplitudes of the control actions from the manipulated variables to the control variables To increase cost effectiveness and/or to reduce byproduct concentration, it is important to reduce purge streams, e.g., the phosgene purge. In general, the process can be set up with or without a small amount of these purges. Preferably the amount of purged phosgene and HCl is controlled by the temperature of the recovery unit. It has been found that the temperature can be controlled independently of the concentration and level control of the phosgene solution. This leads to an easily designed and stable control. Most preferably, an emergency control is provided for the phosgene purge to safeguard that no more phosgene and HCl are purged than can be neutralized or eliminated in a connected neutralization/elimination unit. For that reason, after a first predetermined amount of purged phosgene has been exceeded, the phosgene stream and the amount of the solvent feed stream are controlled to adjust the amount of purged phosgene to a level below a second predetermined amount of purged phosgene. The master control strategy for the general operation in accordance with the present invention in which the amount of the phosgene stream and the amount of the solvent feed stream can be controlled to adjust the concentration and the level of the recovery unit or the solution tank, which in turn controls the exit stream, can be overridden for a while until the amount of purged phosgene is reduced to an acceptable value. Normally, any emergency operation is short-lived, so that disturbances to the amount and quality of the exit stream are low or even equalized by the other subunits of the production process.

It is preferred that the phosgene be produced on-site of the isocyanate production facility. Hence, a phosgene production unit for providing the phosgene stream may be included in the isocyanate production facility. The phosgene production unit can be fed by a CO stream composed mainly of CO and a $Cl_2$ stream composed mainly of $Cl_2$. CO and $Cl_2$ may be produced on-site as well. For example, $Cl_2$ may be produced by electrolysis of brine and/or aqueous HCl or by the Deacon process, that is, by oxidation of gaseous HCl with oxygen or an oxygen-containing gas (e.g., air) using a catalyst. CO can be produced using a reformer or by partial oxidation of coke. Most preferably, a control strategy is provided for the phosgene production unit which prevents free $Cl_2$ in the phosgene stream as much as possible. Therefore, the amount of the phosgene stream and/or the amount of the CO stream and/or the amount of the $Cl_2$ stream is controlled independently of the target amount of phosgene for the reactor in case chlorine is detected in the phosgene stream.

In order to reduce dynamic effects which may lead to major disturbances, it may be advantageous to provide buffers, e.g., tanks connected to the streams. Preferably the buffering effects of the subsystems of the isocyanate production process are used. For example, a distillation column provides a buffering effect because the level of the distillation column (i.e., the ratio of liquid to gaseous components) is variable, so that more or less feed can be stored in the distillation column just by closing or opening output valves. Thus, it is preferred that a level control is provided for at least part of a unit of a subsystem such as the recovery unit and/or the reactor and/or the separator. The level control comprises a standard level control and a disturbance level control, which is more strongly amplified than the standard level control. The level control is based on the disturbance level control when a first predetermined upper limit of the level is exceeded and/or a first predetermined lower limit of the level is below target.

The level control is based on the standard level control when a second predetermined upper limit of the level is below target and/or a second predetermined lower limit of the level is exceeded. Thus, it is possible that the output of a given subsystem or section of a unit of the subsystem is nearly constant independent of disturbing oscillations in the feed. This ensures that the output amount follows slowly to the new optimized value when the feed amount changes to another amount. At the same time, it is ensured that the subsystem or the section of the subsystem does not run empty or overflow due to the slow adjustments because the amplification increases and the correction of the output amount occurs faster above the upper limit and below the lower limit. Since the solvent can be fed to the solvent feed stream as well as to the amine solution stream, it is preferred that the resource stream which comprises mainly solvent is fed to the solvent feed stream and/or to the amine solution stream via a buffer tank.

Figure 1:
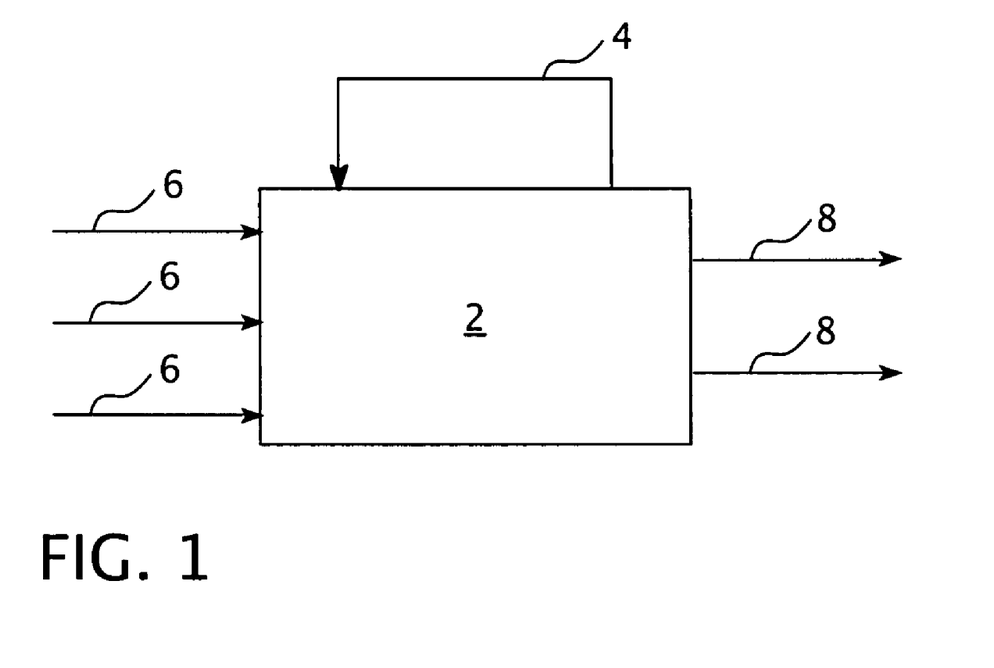
FIG. 1 is a schematic simplified block diagram of an isocyanate production facility.

The isocyanate production process is illustrated in FIG. 1 in simplified form. In FIG. 1, the isocyanate facility 2 includes an inner recycling stream 4. Several incoming streams 6 are fed to the isocyanate facility 2. The incoming streams 6 may be composed of amine, solvent or phosgene. Several exit streams 8 leave the isocyanate facility 2. The exit streams 8 may be composed of the wanted product (i.e., isocyanate), which may be provided in different qualities. For example, one of the exit streams 8 may be made up of a monomeric isocyanate with a specific structure and the other exit stream 8 may be composed of a mixture of isocyanates having different molecular weights. Additional outgoing streams may also be provided (e.g., a purge) not illustrated in FIG. 1. Due to the inner recycling stream 4, the control of the isocyanate facility 2 and the isocyanate production process performed by the isocyanate facility 2 is very difficult, because almost every process parameter has an impact on the amount and the quality of the exit streams 8.

Figure 2:
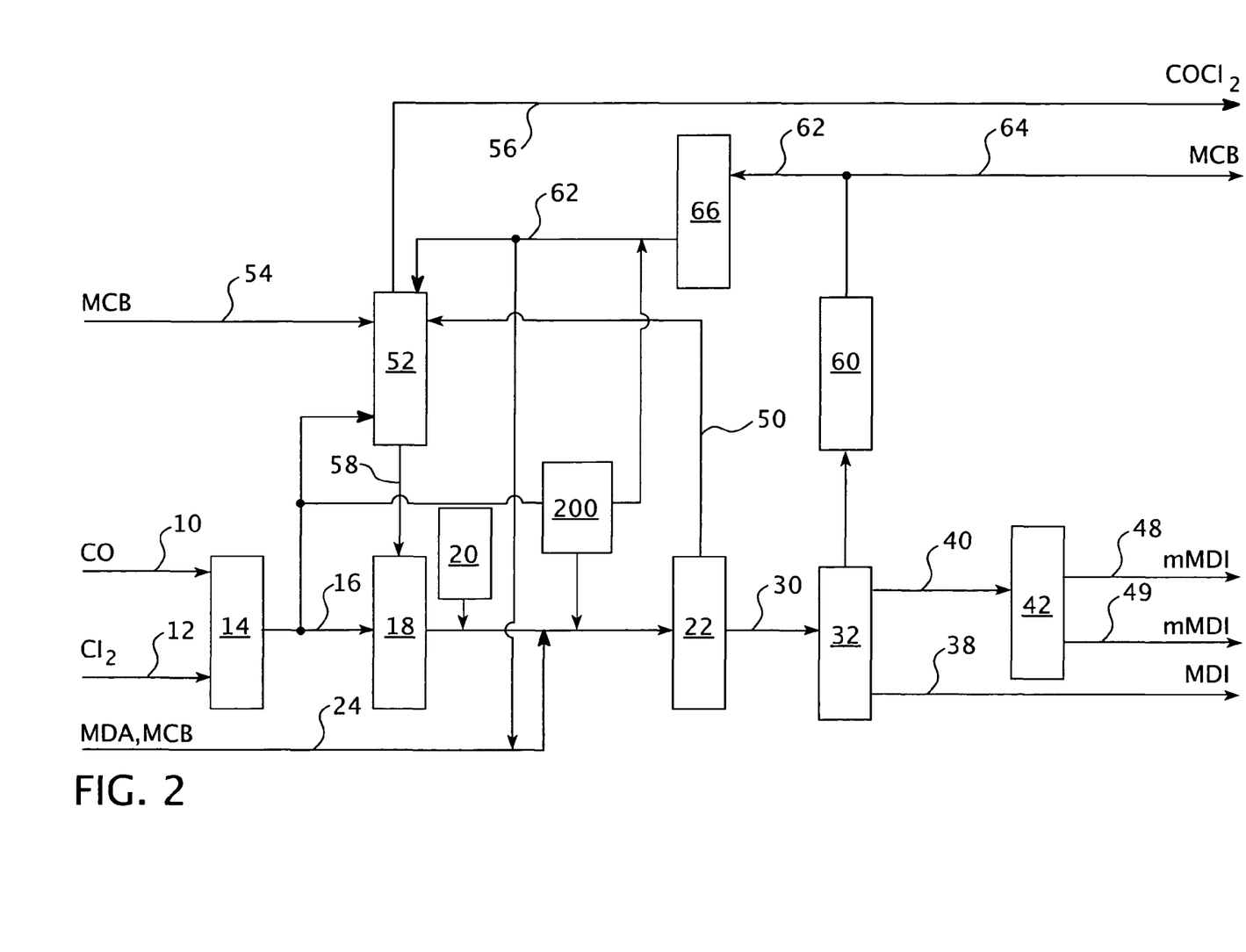
FIG. 2 is a schematic simplified block diagram of an isocyanate production process of an isocyanate production facility.

The isocyanate production process is illustrated in more detail in FIG. 2 and will be described, by way of an example, in terms of the production of MDI (diphenylmethane diisocyanate) by reacting phosgene (COCl$_2$) and MDA (diphenylmethane diamine) dissolved in MCB (monochlorobenzene). In the MDI production process shown in FIG. 2, a CO stream 10 and a Cl$_2$ stream 12 are fed to a phosgene generation unit 14. A phosgene stream 16 is fed from the phosgene generation unit 14 to a solution unit 18 in which the phosgene is dissolved in MCB. A phosgene solution stream 20 is fed from the solution unit 18 to a reactor 22. An amine solution stream 24 composed of MDA dissolved in MCB is fed to the phosgene solution stream 20 before the combined stream 200 enters the reactor 22. It is further possible to feed stream 24 directly to reactor 22. It is also possible that the reactor 22 is made up of more than one subunit so that the MDI can be produced in more than one step. A product stream 30 composed primarily of MDI and MCB is fed from the reactor 22 to a separator unit 32. The separator 32 may be made up of several subunits in sequence and/or in parallel (not illustrated in FIG. 2 for the sake of clarity). A first exit stream 38 from the separator 32 leaves the production system for shipping or storing. The first exit stream 38 is primarily composed of polymeric MDI, that is, a mixture of isocyanates of the diphenylmethane series as depicted in the following formula:

$$x = 2 \ldots n$$

A second exit stream 40 from the separator 32 is primarily composed of monomeric MDI, that is a mixture of isocyanates of the diphenylmethane series as shown above, where x=2. In order to receive monomeric MDI the second exit stream 40 is fed to an isomer separation unit 42. The isomer separation unit 42 may be made up of several subunits in sequence and/or in parallel to further separate monomeric MDI isomers. A third exit stream 48 and a fourth exit stream 49 each composed mainly of a specific monomeric MDI isomer (mMDI) leave the production system.

A recycle stream 50 from the reactor 22 is composed mainly of excess phosgene, solvent, HCl and inert materials from the reactor. The recycle stream 50 is fed to a recovery unit 52. Thus, the recycle stream 50 is an inner recycling stream of the isocyanate production process. In the recovery unit 52, most of the phosgene is dissolved in MCB being fed to the recovery unit 52 from a solvent feed stream 54. Phosgene that is not dissolved in the fed MCB as well as impurities or side products like HCl leave the recovery unit 52 by means of a phosgene purge 56 for annihilation. The recovered phosgene leaves the recovery unit 52 in a recovery stream 58 which is fed to the solution unit 18. It is further possible that the recovery stream be fed to stream 20 and/or to the reactor 22.

Although it is not necessary, where the structural design of the isocyanate facility makes it possible, it is preferred to feed a stream indirectly to its designated unit. For example, in FIG. 2, indirect feeding of the phosgene stream 16 is illustrated. If the phosgene generation unit 14 is located near the recovery unit 52, it may be preferred to feed the phosgene of the phosgene stream 16 to the recovery unit 52, the recycle stream 50 and/or the resource stream 62 so that the phosgene stream is indirectly fed to the solution unit 18. A person skilled in the art will readily appreciate other advantageous possibilities for an indirect feeding of further streams. For example, the solvent feed stream 54 may be fed first to the buffer tank 66 and the like.

The weight ratio of amine to solvent in stream 200 to the reaction unit 22 is preferably less than or equal to 10, preferably $\geq 2$ and $\leq 8$ and most preferably $\geq 2$ and $\leq 7$. The content of amine in the amine solution stream 24 is $\geq 15\%$ and $\leq 95\%$, preferably $\geq 15\%$ and $\leq 85\%$ by weight based on the combined weight of solvent and amine in this stream.

In the separator 32, MDI and MCB are separated, e.g., by means of several distillation columns. The separated gaseous MCB is fed to a condenser 60 so that the separated MCB is liquid. The liquid MCB can be split in a resource stream 62 to recover the separated MCB and a solvent purge 64, e.g., for annihilating the MCB so that impurities in the MCB do not increase. In the illustrated embodiment, the resource stream 62 is fed to a buffer tank 66 where the MCB can be stored for further use. Moreover, variation to the amount of the resource stream can be equalized by means of the buffer tank 66. The recovered MCB in the buffer tank 66 can be fed to the recovery unit 52 for recovering phosgene and/or to the mixture stream 24 for dissolving MDA. Thus, the resource stream 62 is an inner recycling stream of the isocyanate production process. Residual educts in the recovered MCB are fed back to the reactor so that the residual educts may react further, preferably to form a desired product like MDI.

Figure 3:
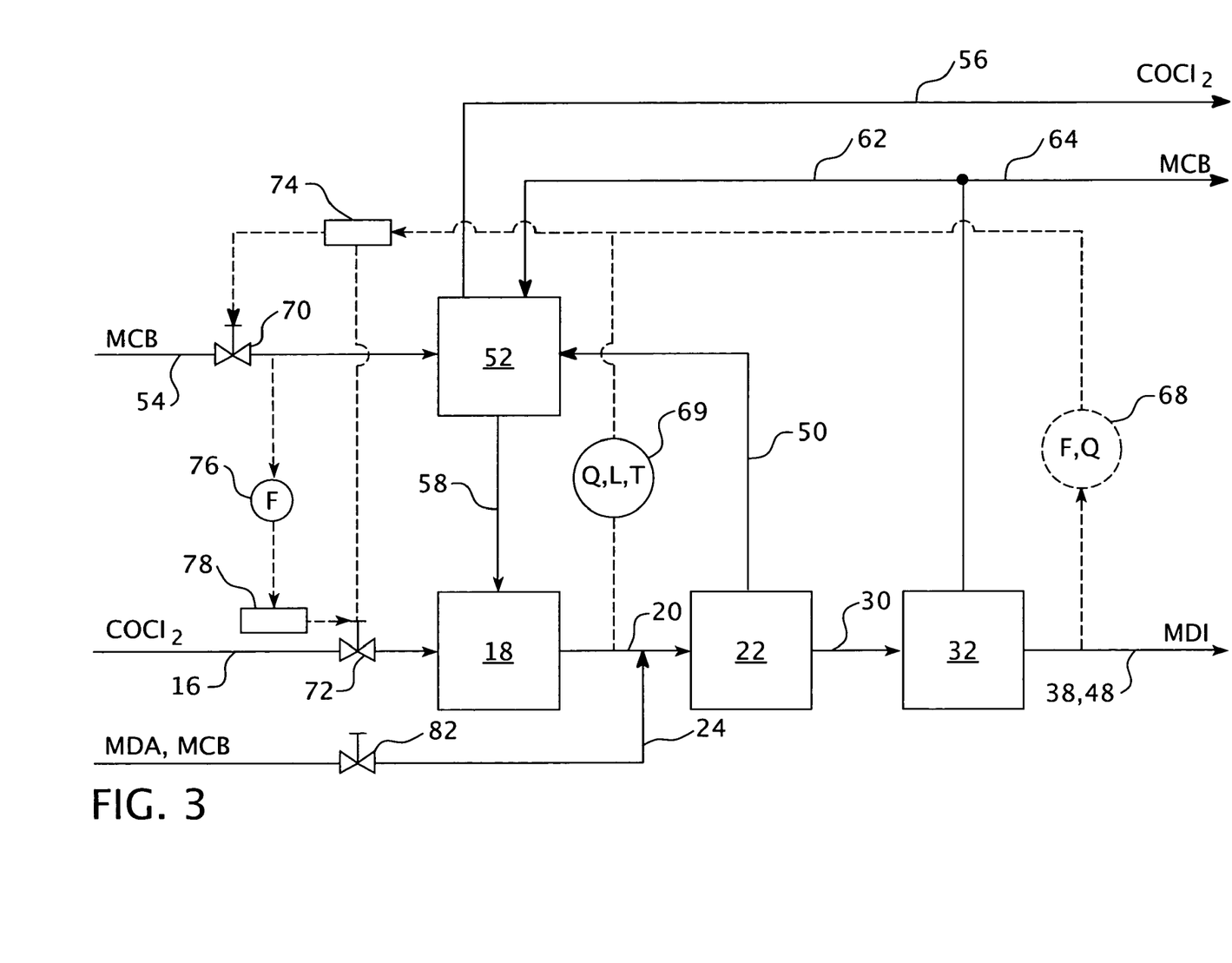
FIG. 3 is a schematic simplified block diagram of the facility diagrammed in FIG. 2 with a supervisory or master control.

As illustrated in FIG. 3, the MDI production process can be controlled by controlling the amount of the solvent feed stream 54 and the phosgene stream 16 based on the amount and quality (concentration) of the at least one exit stream 38, 48. For that purpose, the flow rate (F) and the quality (Q) can be measured by an exit stream measurement device 68 or calculated on the basis of the concentration, the temperature and the level of the solution unit 18 measured by a solution unit measurement device 69. The information about the flow rate and the quality of the exit stream 38, 48 is processed to set a solvent feed stream valve 70 for controlling the amount of the solvent feed stream 54. The same information is used to set a phosgene stream valve 72 for controlling the amount of the phosgene stream 16. The amount of phosgene stream 16 is set based on the amount of the Amine solution stream controlled with valve 82. The correction variable to set the solvent feed stream valve 70 and the phosgene stream valve 72 is provided by a controller 74 for controlling the solvent feed stream 54 and the phosgene stream 16. In order to safeguard the stability of the MDI production process, the flow rate (F) of the solvent feed stream 54 is measured by a solvent feed stream measurement device 76. This allows controlling the flow rate (i.e., the amount of the phosgene stream 16) by means of the phosgene stream valve 72 based on the flow rate or amount of the solvent feed stream 54 or even based on the target flow rate or target amount of the solvent feed stream 54. This control is provided by a controller 78 for controlling the phosgene stream 16.

Figure 4:
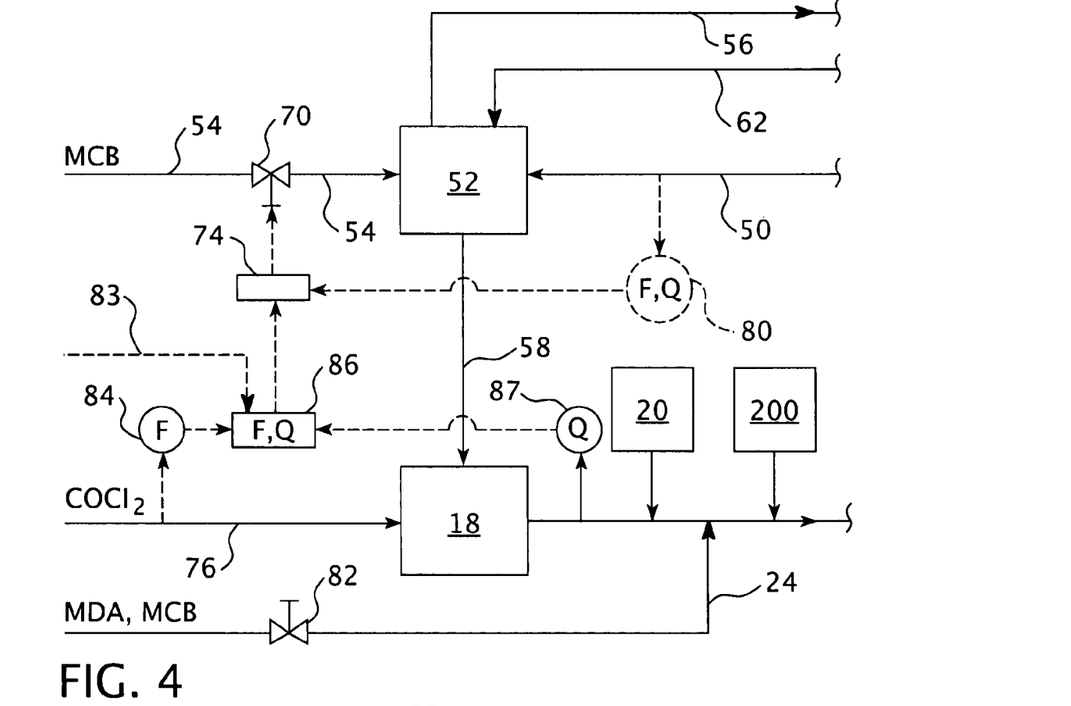
FIG. 4 is a schematic simplified detail of the facility diagrammed in FIG. 3 with a regulatory control.

Since the control of the phosgene in the solution unit 18 is strongly coupled, a multivariable controller or a similar structure has to be designed to control the system. The drawback of a classical multivariable controller is realizability in the Distributed Control System (DCS). It is not very easy to design and implement a classical multivariable controller into the DCS. To avoid a multivariable controller, a different structure using additional process knowledge is preferred (FIG. 4). To control the concentration of the phosgene in the solution unit 18, the amount of phosgene disturbing the system can be calculated in a calculation unit 86. The phosgene fed to the solution unit 18 can be calculated from the amount of phosgene in the phosgene stream 16 produced in the phosgene generation unit 14. It is sufficient to measure the flow rate (amount) of the phosgene stream 16 by means of a phosgene stream measurement device 84. In the alternative, it is possible to measure the phosgene concentration in stream 20 by means of a measurement device 87. The amount of phosgene coming back from the reactor 22 can be calculated from the MDA-load and the phosgene excess. The amount of MDA can be derived from the preset value of a mixture stream valve 82. This information and other mainly fixed facts are processed via an information input line 83 in the calculation unit 86. Of course, the dynamic behavior of these phosgene amounts have to be taken into account. The sum of the phosgene coming from the phosgene generation unit 14 and the recycle stream 50 can be integrated into the phosgene concentration control action for controlling the solvent feed stream valve 70 via the controller 74. The result is a more simple structure which performs like a multivariable controller and renders a recycle stream measurement device 80 for measuring flow rate (F) and concentration (Q) of the recycle stream 50 unnecessary.

Figure 5:
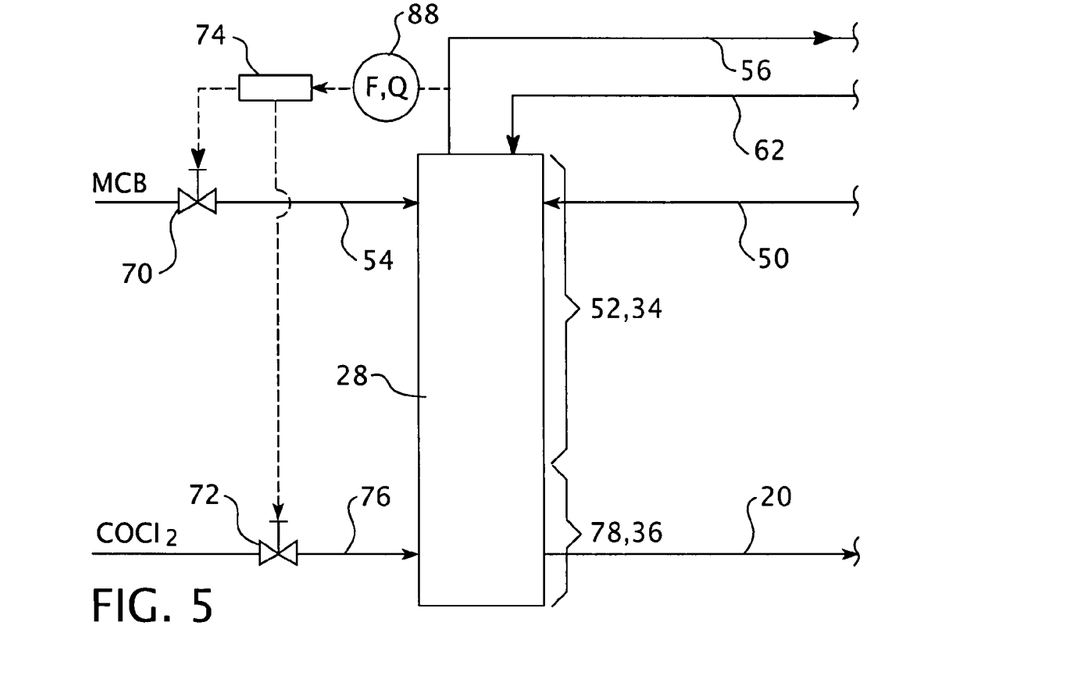
FIG. 5 is a schematic simplified detail of the facility diagrammed in FIG. 3 with another regulatory control.

Since too high of an amount of phosgene and HCl in the phosgene purge 56 may endanger the neutralization/removal of the phosgene and HCl, an override control can be provided (FIG. 5). A phosgene purge measurement device 88 is provided to measure the amount and/or the quality of the phosgene purge 56. If it is detected that the phosgene/HCl neutralization/removal may be endangered, the general control of the master controller 74 is overridden until the danger is eliminated. For that purpose, it is preferred to open the solvent feed stream valve 70.

In the embodiment of the invention illustrated in FIG. 5, the recovery unit 52 and the solution unit 18 are integrated into a single absorber unit 28 made up of an absorber bed section 34 and an absorber bottom 36. Since the recovery of the phosgene is performed in the absorber bed section 34, the absorber bed section 34 is the recovery unit 52 at the same time. Since the solution of the produced phosgene in MCB is performed in the absorber bottom 36, the absorber bottom 36 acts as the solution unit 18 at the same time. The recovery stream is located within the absorber 28 between the absorber bed section 34 and the absorber bottom 36. Thus, it is possible to combine two different functions into one device. For example, the solution unit 18 can be integrated into the reactor 22 in which stream 20 is an inner stream of the reactor 22 composed of several subunits, if necessary.

Figure 6:
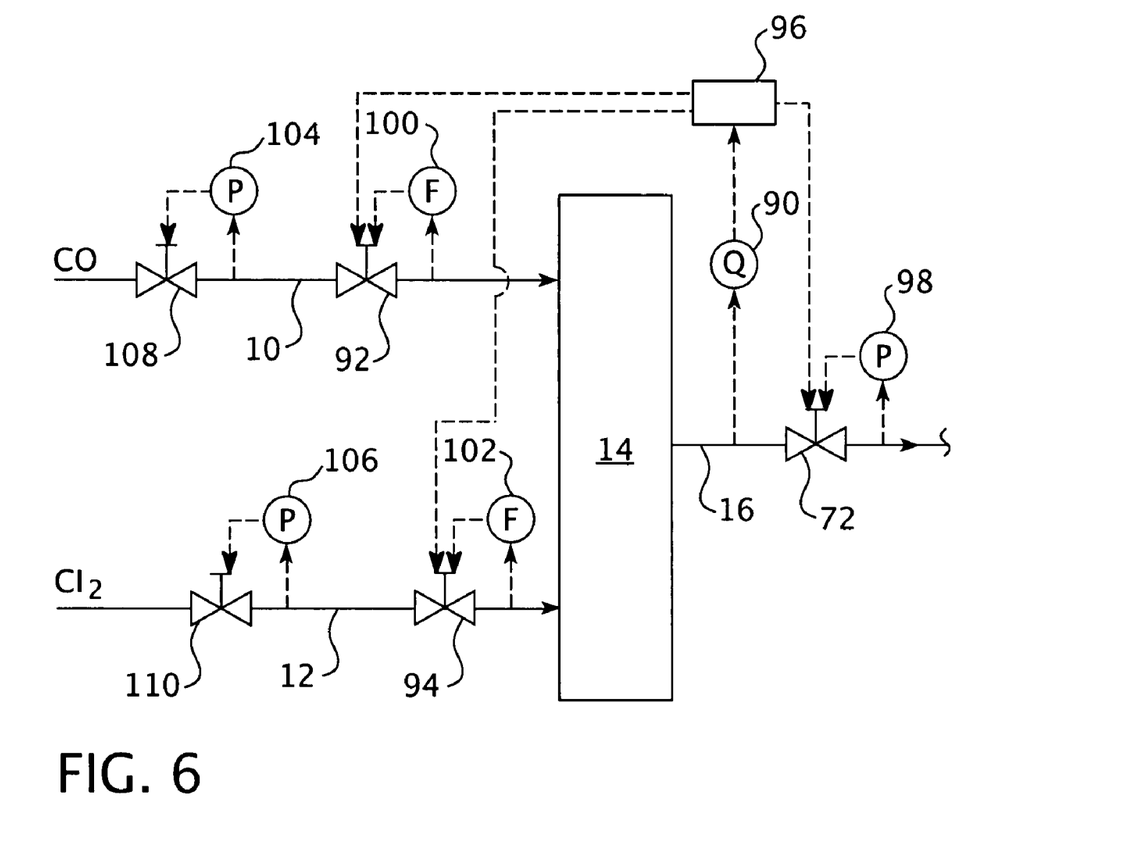
FIG. 6 is a schematic simplified detail of the facility diagrammed in FIG. 3 with another regulatory control.

In order to prevent having $Cl_2$ in the phosgene stream 16, the phosgene stream 16 is monitored for $Cl_2$ by means of an additional phosgene stream measurement device 90 in the phosgene generation unit 14 (FIG. 6). If $Cl_2$ is detected, the phosgene stream valve 72 and/or a CO stream valve 92 and/or a $Cl_2$ stream valve 94 are set by a controller 96 to prevent $Cl_2$ in the phosgene stream 16. By means of the controller 96 the valves 72, 92, 94 are controlled so, that the amount of the phosgene stream 16 made up of $Cl_2$ is reduced and/or the phosgene production is increased by increasing the flow rate of the CO stream 10 and/or reducing the flow rate of the $Cl_2$ stream. Preferably only the CO stream valve 92 is set by the controller 96. The further phosgene stream measurement device 90 is able to determine the CO concentration in the phosgene stream 16 so that in the general mode the quality of the phosgene stream 16 can be monitored by means of the additional phosgene stream measurement device 90.

Since the pressure of the phosgene stream 16 affects the pressure in nearly all units of the isocyanate production process, the pressure of the phosgene stream 16 is monitored by a phosgene pressure measurement device 98 for controlling the pressure via the phosgene stream valve 72. In order to provide the intended flow rate of phosgene, a CO feed measurement device 100 is provided in the CO stream 10 and a $Cl_2$ feed measurement device 102 is provided in the $Cl_2$ stream 12. By means of the CO feed measurement device 100 and the $Cl_2$ feed measurement device 102, the CO stream valve 92 and the $Cl_2$ stream valve 94 are controlled to provide the phosgene generation unit 14 with sufficient educts. Since the flow rate of CO and $Cl_2$ depends on their pressure, a pre-pressure control is provided. By means of a CO pressure measurement device 104 and a $Cl_2$ pressure measurement device 106, a CO pressure valve 108 and a $Cl_2$ pressure valve 110 are controlled. The measured pressures and flow rates are strongly coupled to each other so that adjusting one of the valves 72, 92, 94, 108, or 110 may lead to an oscillating state of the phosgene production unit 14 rendering the phosgene production unstable. In order to prevent unstable situations, the controller for controlling the valves 72, 92, 94, 108, 110 includes a time constant for adjusting the speed of each controller. The selection of appropriate time constants provides controllers that may each set its dedicated valve 72, 92, 94, 108, 110 faster or slower with respect to the other controllers. A good selection of the time constants using common methods known to people skilled in the art leads to a decoupling and thus to a facilitated control. For example, the CO pressure valve 108 and the $Cl_2$ pressure valve 110 are set faster with respect to the other valves 72, 92, 94 in which the CO pressure valve 108 is adjusted more quickly than the $Cl_2$ pressure valve 110. Accordingly, the CO stream valve 92 and the $Cl_2$ stream valve 94 are set faster with respect to the phosgene stream valve 72 in which the CO stream valve 92 is adjusted faster than the $Cl_2$ stream valve 94. This kind of decoupling can be adapted to the other units or subunits of the isocyanate production process.

Figure 7:
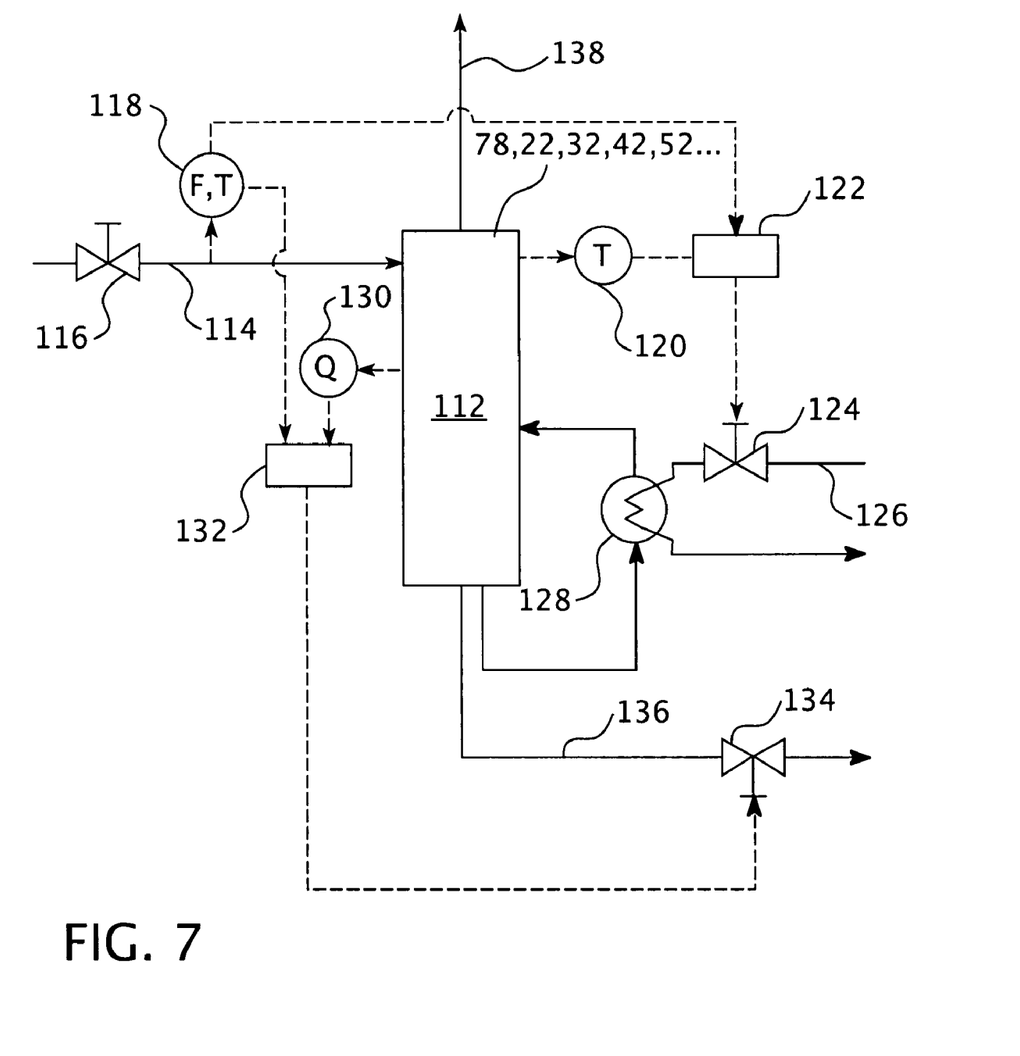
FIG. 7 is a schematic simplified detail of the facility diagrammed in FIG. 3 with an example of another regulatory control.

Another possible control, e.g., for the solution unit 18, the reactor 22, the separator 32, the isomer separation unit 42, the recovery unit 52 and the like or one of their subunits is illustrated by way of example in FIG. 7. A unit 112 which may be the solution unit 18, the reactor 22, the separator 32, the isomer separation unit 42, the recovery unit 52 or the like is fed by a feed stream 114 which is usually controlled by a feed valve 116. Normally the flow rate, the temperature and the pressure of the feed stream 114 are known or measured by means of a feed stream measurement device 118. Several process parameters of the unit 112 like concentration, temperature, level or pressure are measured. In order to control the temperature, a temperature measurement device 120 is provided. The temperature of the unit 112 measured by the temperature measurement device 120 as well as the flow rate and temperature of the feed stream 114 are processed in a temperature controller 122. The temperature controller 122 takes the dynamic influence of the feed stream 114 to the temperature of the unit 112 into account so that temperature control in advance is possible. The temperature controller 122 controls a heat valve 124 by which a steam stream 126 is adjusted. The heat stream 126 is fed to a heat exchanger 128 where a part of the fluid of the unit 112 is heated. Cooling can be performed by using a cooling means instead of steam. By means of the temperature control, the concentrations of the fluid in the unit 112 may be controlled. If so, information about the concentrations is processed in the temperature controller 122 for calculating an optimized target temperature. The temperature controller 122 further ensures that a given maximum or minimum temperature is not exceeded. The calculated target temperature is not higher than the maximum temperature and not lower than the minimum temperature.

Accordingly the concentrations of the components in the fluid are controlled. The concentrations are measured by means of a concentration measurement device 130 and processed together with the information about the flow rate of the feed stream 114 in a level controller 132. The level controller 132 takes the dynamic influence of the feed stream 114 on the level and concentration of the unit 112 into account so that advance level and concentration control is possible. The level controller 132 controls output valve 134 by which the output flow rate of an output stream 136 is adjusted. If a further output stream 138 is provided, this further output stream 138 may also be controlled in this manner.

Control of the viscosity of the exit stream 38 is preferred, especially where exit stream 38 is primarily composed of polymeric MDI. For that reason, a viscosity measurement device is provided to measure the viscosity of the exit stream 38. This information is processed in a viscosity controller which controls, e.g., the pressure and temperature of the separator 32.

The particular combinations of elements and features in the above-detailed embodiments are only exemplary; the interchanging and substitution of these teachings with other teachings in this description are also expressly contemplated. As those skilled in the art will recognize variations, modifications, and other implementations of what is described herein without departing from the spirit and the scope of the invention as claimed. Accordingly, the foregoing description is by way of example only and is not intended to be limiting. The invention's scope is defined in the following claims and the equivalents thereto. Furthermore, reference signs used in the description and claims do not limit the scope of the invention as claimed. It is obvious, that the described examples can be applied to the formation of other materials, particularly, other isocyanates such as TDI, HDI, IPDI starting with the corresponding amines like TDA, HDA and using solvents like MCB, ODB etc.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

The invention claimed is:

1. A method for controlling an isocyanate production process conducted in a production facility comprising
   a) at least two incoming streams comprising:
      (1) a phosgene stream comprising phosgene and
      (2) a solvent stream comprising solvent
   b) at least one exit stream containing produced isocyanate and
   c) at least one inner recycling stream comprising adjusting the phosgene stream amount and/or the solvent stream amount by means of regulating controls to control at least one of the at least one exit stream's quality and/or amount and in which the phosgene stream is fed to a solution unit, further comprising:
   I. feeding an amine solution stream comprising a mixture of an amine and a solvent to a phosgene solution stream to form a combined stream comprising amine solution and phosgene solution,
   II. feeding the combined stream to a reactor,
   III. reacting the amine in the combined stream with a molar excess of phosgene based on the amino groups present to form an isocyanate-containing product stream which is fed from the reactor to a separator,
   IV. separating the product stream in the separator into
      (i) at least one exit stream comprising the isocyanate
      (ii) at least one resource stream comprising solvent, and
      (iii) a recycle stream comprising mainly phosgene and/or HCl,
   V. feeding the recycle stream and the solvent stream to a recovery unit for recovering phosgene, to form a recovery stream comprising phosgene and solvent, and
   VI. feeding the recovery stream from the phosgene recovering unit to the solution unit.

2. The method of claim 1 in which the solution unit, the reactor, the separator, the recovery unit and an isomer distillation unit are controlled mainly independently of each other.

3. The method of claim 1 in which the solvent stream amount is adjusted prior to and/or faster than adjustment of the phosgene stream amount, based on amount of the amine solution stream.

4. The method of claim 1 in which the solvent stream amount is adjusted by the regulating controls based on the phosgene stream concentration, amount of phosgene in the recycle stream and amount of produced phosgene.

5. The method of claim 1 in which the phosgene amount in the at least one exit stream and the solvent concentration in the at least on exit stream are kept constant by means of regulatory controls for the at least one exit stream's temperature and pressure.

6. The method of claim 1 in which the solution unit comprises:
   (a) a first solution unit control comprising:
      (i) a solvent concentration control for controlling the solvent concentration in the first solution unit based on a change in amount of the solvent stream and
      (ii) a control for solvent level in the first solution unit, based on a change in amount of the phosgene stream and
   (b) a second solution unit control comprising:
      (i) a solvent concentration control for controlling solvent concentration in the second solution unit, based on a change in amount of the phosgene stream and
      (ii) a control for solvent level in the second solution unit based on a change in amount of the solvent stream,
   in which calculation of target changes in solvent concentration and target level of solution in the solution unit is based upon frequency of change in amount of the solvent stream and/or change in amount of the phosgene stream.

7. The method of claim 1 in which the phosgene recovering unit's temperature is used to control amount of phosgene purged from the solution unit.

8. The method of claim 1 in which the phosgene stream and the resource stream are adjusted after a first predetermined amount of purged phosgene is exceeded and until the amount of purged phosgene falls below a second predetermined amount of purged phosgene.

9. The method of claim 1 in which a CO stream comprising mainly CO and a $Cl_2$ stream comprising mainly $Cl_2$ are fed to a phosgene production unit which provides the phosgene stream and in which the amount of the phosgene stream and/or the amount of the CO stream and/or the amount of the $Cl_2$ stream is controlled independently of a target amount of phosgene for the production facility.

10. The method of claim 1 in which a level control is provided for at least a section of the recovery unit and/or of a reactor and/or of a separator, the level control comprising a standard level control and a disturbance level control, wherein the disturbance level control is more strongly amplified than the standard level control.

11. The method of claim 10 in which the level control is based on the disturbance level control when a first predetermined upper limit is exceeded and/or a first predetermined lower limit is below target.

12. The method of claim 10 in which the level control is based on the standard level control when a second predetermined upper limit is below target and/or a second predetermined lower limit is exceeded.

13. The method of claim 1 in which the resource stream is fed to the solvent stream and/or to the amine solution stream via a buffer tank.

14. The method of claim 1 in which the amine is present in the amine solution stream in an amount of from 15 to 95% by weight, based on combined weight of the solvent and the amine in this stream.

15. The method of claim 1 in which the amine is present in the amine solution stream in an amount of from 15 to 85% by weight, based on combined weight of the solvent and the amine in this stream.

16. The method of claim 1 in which the phosgene is present in the phosgene solution stream in an amount $\geq 15\%$ by weight, based on combined weight of the solvent and the phosgene in this stream.

17. The method of claim 1 in which the phosgene is present in the phosgene solution stream in an amount $\geq 20\%$ by weight, based on combined weight of the solvent and the phosgene in this stream.

18. The method of claim 1 in which the phosgene is present in the phosgene solution stream in an amount $\geq 30\%$ by weight, based on combined weight of the solvent and the phosgene in this stream.

19. The method of claim 1 in which weight ratio of solvent to amine in the combined stream is $\leq 10$.

20. The method of claim 1 in which weight ratio of solvent to amine in the combined stream is $\leq 8$.

21. The method of claim 1 in which weight ratio of solvent to amine in the combined stream is $\geq 2$ and $\leq 7$.

22. A method for controlling an isocyanate production process in a production facility comprising:
   a) at least two incoming streams comprising:
      (1) a phosgene stream comprising phosgene and
      (2) a solvent stream comprising a solvent,
   b) at least one exit stream and
   c) at least one inner recycling stream,
the method comprising:
   I. feeding the phosgene stream to a solution unit to obtain a phosgene solution stream,
   II. feeding an amine solution stream comprising a mixture of an amine and a solvent to a phosgene solution stream to form a combined steam,
   III. feeding the combined stream to a reactor,
   IV. reacting the amine solution stream with the phosgene solution stream to form an isocyanate-containing product stream which is fed from the reactor to a separator,
   V. separating the product stream in the separator into
      (i) at least one exit stream comprising the isocyanate,
      (ii) at least one resource stream comprising solvent, and
      (iii) a recycle stream comprising mainly phosgene and/or HCl,
   VI. feeding the recycle stream and the solvent stream to a recycle stream of a recovery unit for recovering phosgene to form a recovery stream comprising phosgene and solvent, and
   VII. feeding the recovery stream from the phosgene recovering unit to the solution unit
in which
   A. the solution unit, the reactor, the separator, the recovery unit and an isomer distillation unit are controlled mainly independently of each other,
   B. the solvent stream amount is adjusted prior to and/or faster than adjustment of the phosgene solution stream amount which is changed based on amount of the amine solution stream,
   C. the solvent stream amount is adjusted by a controller on the basis of phosgene solution concentration, amount of phosgene in the recycling stream and amount of produced phosgene,
   D. solution control is conducted by
      (a) a first solution unit control comprising:
         (i) a solvent concentration control for controlling the solvent concentration in the first solution unit based on a change in amount of the solvent stream and (ii) a control for solvent level in the first solution unit based on change in amount of the phosgene stream and
(b) a second solution unit control comprising
(i) a solvent concentration control for controlling the solvent concentration in the second solution unit based on change in amount of phosgene stream and
(ii) a control for solvent level in the second solution unit based on a change in amount of the solvent stream, and in which calculation of target changes in solvent concentration and target level of solution in the solution unit is based on frequency of change in the amount of the solvent stream and/or of change in amount of the phosgene stream,
E. amount of phosgene in the recycle stream and concentration of the solvent in the recycle stream are kept constant by means of controls which regulate temperature and pressure of the recycle stream,
F. the phosgene recovery unit's temperature is used to control amount of phosgene purged from the solution unit,
G. the phosgene stream and the resource stream are adjusted after a first predetermined amount of purged phosgene is exceeded and until the amount of purged phosgene falls below a second predetermined amount of purged phosgene,
H. a CO stream comprising mainly CO and a $Cl_2$ stream comprising mainly $Cl_2$ are fed to a phosgene production unit which provides the phosgene stream and the amount of the phosgene stream and/or the amount of the CO stream and/or the amount of the $Cl_2$ stream is controlled independently of a target amount of phosgene for the reactor,
I. a level control is provided for at least a section of the phosgene recovery unit and/or of the reactor and/or of a separator, the level control comprising a standard level control and a disturbance level control, wherein the disturbance level control is more strongly amplified than the standard level control,
J. the level control is based on the disturbance level control when a first predetermined upper limit of the level is exceeded and/or a first predetermined lower limit of the level is below target,
K. the level control is based on the standard level control when a second predetermined upper limit of the level is below target and/or a second predetermined lower limit of the level is exceeded,
L. the resource stream is fed to the solvent stream and/or to the mixture stream via a buffer tank,
M. the amine is present in the mixture stream in an amount of from 15 to 40% by weight, based on total weight of the mixture stream.

23. The method of claim 22 in which the amine is present in the amine solution stream in an amount of from 15 to 95% by weight, based on combined weight of the solvent and the amine in this stream.

24. The method of claim 22 in which the amine is present in the amine solution stream in an amount of from 15 to 85% by weight, based on combined weight of the solvent and the amine in this stream.

25. The method of claim 22 in which the phosgene is present in the phosgene solution stream in an amount of from $\geq 15\%$ by weight, based on combined weight of the solvent and the phosgene in this stream.

26. The method of claim 22 in which the phosgene is present in the phosgene solution stream in an amount of from a $\geq 20\%$ by weight, based on combined weight of the solvent and the phosgene in this stream.

27. The method of claim 22 in which the phosgene is present in the phosgene solution stream in an amount of from $\geq 30\%$ by weight, based on combined weight of the solvent and the phosgene in this stream.

28. The method of claim 22 in which the weight ratio of solvent to amine in the combined stream is $\leq 10$.

29. The method of claim 22 in which the weight ratio of solvent to amine in the combined stream is $\leq 8$.

30. The method of claim 22 in which the weight ratio of solvent to amine in the combined stream is $\geq 2$ and $\leq 7$.

31. An isocyanate production facility comprising:
a) at least two incoming streams comprising:
(1) a phosgene stream comprising phosgene and
(2) a solvent stream comprising solvent
b) at least one exit stream containing produced isocyanate,
c) at least one inner recycling stream,
d) regulating controls for adjusting the phosgene stream amount and/or the solvent stream amount to control at least one of the at least one exit stream's quality and/or amount,
e) means for feeding the phosgene stream to a solution unit to obtain a phosgene solution stream,
f) means for feeding an amine solution stream comprising a mixture of an amine and a solvent to a phosgene solution stream to form a combined stream,
g) means for feeding the phosgene solution stream from the solution unit to a reactor,
h) a reactor for reacting the phosgene solution stream with the amine solution stream to form an isocyanate-containing product stream which is fed from the reactor to
i) a separator for separating the product stream in the separator into
(1) at least one exit stream comprising the isocyanate,
(2) at least one resource stream comprising solvent, and
(3) a recycle stream comprising mainly phosgene and/or HCl,
j) means for feeding the recycle stream and the solvent stream to a recovery stream of
k) a recovery unit for recovering phosgene, and
l) means for feeding the recovery stream from the phosgene recovering unit to the solution unit.

32. The facility of claim 31 in which the solution unit, the reactor, the separator, the recovery unit and an isomer distillation unit are controlled mainly independently of each other.

33. The facility of claim 31 in which the amount of the solvent stream is adjusted prior to and/or faster than adjustment of the amount of the phosgene stream.

34. The facility of claim 31 in which the solvent stream amount is changed on the basis of the amount of the produced phosgene calculated by using variation in time and amount produced in phosgene generation.

35. The facility of claim 31 in which solution control is conducted by
(a) a first solution unit control comprising:
(i) a control for solvent concentration in a first solution unit based on change in amount of the solvent stream and
(ii) a control of the first solution unit level based on a change in amount of the phosgene stream and
(b) a second solution unit control comprising:
(i) a control for the solvent concentration in the second solution unit based on a change in amount of the phosgene stream and
(ii) a control of the second solution unit level based on a change in amount of the solvent stream, in which calculation of target changes in solvent concentration and target level of solution in the solution unit is based on frequency of change in amount of the solvent stream and/or of the change in amount of the phosgene stream.

36. The facility of claim 35 in which level control is based on standard level control when a second predetermined upper limit of a level being controlled is below target and/or a second predetermined lower limit of the level being controlled is exceeded.

37. The facility of claim 31 in which amount of purged phosgene is controlled by the recovery unit's temperature.

38. The facility of claim 31 in which the phosgene stream and the resource stream are adjusted after a first predetermined amount of purged phosgene is exceeded until the purged phosgene amount falls below a second predetermined amount of purged phosgene.

39. The facility of claim 31 in which a CO stream comprising mainly CO and a $Cl_2$ stream comprising mainly $Cl_2$ are fed to a phosgene production unit which provides the phosgene stream for the isocyanate production and in which the amount of the phosgene stream and/or the amount of the CO stream and/or the amount of the $Cl_2$ stream is/are controlled independently of a target amount of phosgene for the reactor.

40. The facility of claim 31 in which a level control is provided for at least a section of a recovery unit and/or of a reactor and/or of a separator, the level control comprising a standard level control and a disturbance level control, wherein the disturbance level control is more strongly amplified than the standard level control.

41. The facility of claim 40 in which the level control is based on the disturbance level control when a first predetermined upper limit of the level is exceeded and/or a first predetermined lower limit of the level is below target.

42. The facility of claim 31 in which the resource stream is fed to the solvent stream and/or to the mixture stream via a buffer tank.

* * * * *